(12) United States Patent
Bogart et al.

(10) Patent No.: US 8,864,776 B2
(45) Date of Patent: Oct. 21, 2014

(54) DEPLOYMENT SYSTEM FOR SURGICAL SUTURE

(75) Inventors: Michael Bogart, Milford, CT (US); Gregg Krehel, Newtown, CT (US); Christopher Fishbein, Wolcott, CT (US); Russell Pribanic, New Milford, CT (US); David Kirsch, Madison, CT (US); Kenneth W. Horton, Jr., South Glastonbury, CT (US); Timothy D. Kosa, Hamden, CT (US); Nicholas Maiorino, Branford, CT (US); Mark S. Buchter, Ansonia, CT (US); William R. Bowns, Ansonia, CT (US)

(73) Assignee: Covidien LP, Mansfield, MA (US)

( * ) Notice: Subject to any disclaimer, the term of this patent is extended or adjusted under 35 U.S.C. 154(b) by 720 days.

(21) Appl. No.: 12/415,288

(22) Filed: Mar. 31, 2009

(65) Prior Publication Data
US 2009/0259233 A1    Oct. 15, 2009

Related U.S. Application Data (60) Provisional application No. 61/123,900, filed on Apr. 11, 2008.

(51) Int. Cl.
*A61B 17/04*     (2006.01)
*A61B 17/062*    (2006.01)
*A61B 17/06*     (2006.01)

(52) U.S. Cl.
CPC ... *A61B 17/06004* (2013.01); *A61B 2017/0609* (2013.01); *A61B 2017/06047* (2013.01); *A61B 2017/06176* (2013.01); *A61B 17/0625* (2013.01); *A61B 17/0469* (2013.01)
USPC ............................. 606/144; 606/226; 606/228

(58) Field of Classification Search
CPC .................. A61B 17/06004; A61B 17/06166; A61B 2017/06047
USPC .......................... 606/139, 144–147, 222–231
See application file for complete search history.

(56) References Cited

U.S. PATENT DOCUMENTS

| 1,822,330 | A | 9/1931 | Ainslie |
| 2,327,353 | A | 8/1943 | Karle |

(Continued)

FOREIGN PATENT DOCUMENTS

| DE | 44 23 881 C1 | 10/1995 |
| EP | 0 592 244 A2 | 4/1994 |

(Continued)

OTHER PUBLICATIONS

European Search Report for EP 09251065.0-2310 date of completion is Aug. 4, 2009 (4 pages).

(Continued)

*Primary Examiner* — Gregory Anderson (57) ABSTRACT

A suture deployment system is disclosed including a surgical needle having a flexible suture fixedly attached thereto and a target suture releasably secured to the flexible suture. A collar is positioned between the flexible suture and the target suture and is fixedly secured to the flexible suture. The target suture is releasably secured to the collar is such that the target suture may detach from the collar once a surgical procedure has been completed. The surgical needle is a double pointed surgical needle specifically configured to be manipulated by a surgical suturing apparatus.

26 Claims, 8 Drawing Sheets

(56) References Cited

U.S. PATENT DOCUMENTS

| | | | |
|---|---|---|---|
| 3,073,311 | A | 1/1963 | Tibbs et al. |
| 3,123,077 | A | 3/1964 | Alcamo |
| 3,311,110 | A * | 3/1967 | Singerman et al. ............ 606/226 |
| 3,716,058 | A | 2/1973 | Tanner, Jr. |
| 4,236,470 | A | 12/1980 | Stenson |
| 4,621,640 | A | 11/1986 | Mulhollan et al. |
| 4,890,615 | A | 1/1990 | Caspari et al. |
| 4,898,156 | A | 2/1990 | Gatturna et al. |
| 4,923,461 | A | 5/1990 | Caspari et al. |
| 4,935,027 | A | 6/1990 | Yoon |
| 4,957,498 | A | 9/1990 | Caspari et al. |
| 5,037,433 | A | 8/1991 | Wilk et al. |
| 5,042,707 | A | 8/1991 | Taheri |
| 5,046,513 | A | 9/1991 | Gatturna et al. |
| 5,080,663 | A | 1/1992 | Mills et al. |
| 5,100,421 | A | 3/1992 | Christoudias |
| 5,100,430 | A | 3/1992 | Aveillanet et al. |
| 5,123,911 | A * | 6/1992 | Granger et al. ................ 606/224 |
| 5,192,303 | A | 3/1993 | Gatturna et al. |
| 5,209,747 | A | 5/1993 | Knoepfler |
| 5,271,543 | A | 12/1993 | Grant et al. |
| 5,300,082 | A | 4/1994 | Sharpe et al. |
| 5,306,290 | A | 4/1994 | Martins et al. |
| 5,308,353 | A | 5/1994 | Beurrier |
| 5,314,446 | A | 5/1994 | Hunter et al. |
| 5,330,502 | A | 7/1994 | Hassler et al. |
| 5,336,229 | A | 8/1994 | Noda |
| 5,350,391 | A | 9/1994 | Iacovelli |
| 5,358,498 | A | 10/1994 | Shave |
| 5,358,511 | A | 10/1994 | Gatturna et al. |
| 5,374,277 | A | 12/1994 | Hassler |
| 5,387,221 | A | 2/1995 | Bisgaard |
| 5,389,103 | A | 2/1995 | Melzer et al. |
| 5,391,176 | A | 2/1995 | de la Torre |
| 5,403,342 | A | 4/1995 | Tovey et al. |
| 5,405,352 | A | 4/1995 | Weston |
| 5,439,478 | A | 8/1995 | Palmer |
| 5,454,823 | A | 10/1995 | Richardson et al. |
| 5,454,827 | A | 10/1995 | Aust et al. |
| 5,472,446 | A | 12/1995 | de la Torre |
| 5,478,344 | A | 12/1995 | Stone et al. |
| 5,480,406 | A | 1/1996 | Nolan et al. |
| 5,496,334 | A | 3/1996 | Klundt et al. |
| 5,500,000 | A | 3/1996 | Feagin et al. |
| 5,527,323 | A | 6/1996 | Jervis et al. |
| 5,540,703 | A | 7/1996 | Barker, Jr. et al. |
| 5,540,706 | A | 7/1996 | Aust et al. |
| 5,549,617 | A | 8/1996 | Green et al. |
| 5,549,637 | A | 8/1996 | Crainich |
| 5,554,171 | A | 9/1996 | Gatturna et al. |
| 5,562,686 | A | 10/1996 | Sauer et al. |
| 5,564,615 | A | 10/1996 | Bishop et al. |
| 5,571,090 | A | 11/1996 | Sherts |
| 5,573,286 | A | 11/1996 | Rogozinski |
| 5,575,799 | A | 11/1996 | Bolanos et al. |
| 5,582,617 | A | 12/1996 | Klieman et al. |
| 5,591,181 | A | 1/1997 | Stone et al. |
| 5,601,224 | A | 2/1997 | Bishop et al. |
| 5,620,415 | A | 4/1997 | Lucey et al. |
| 5,628,756 | A | 5/1997 | Barker, Jr. et al. |
| 5,630,825 | A | 5/1997 | de la Torre et al. |
| 5,632,751 | A | 5/1997 | Piraka |
| 5,643,293 | A | 7/1997 | Kogasaka et al. |
| 5,643,294 | A | 7/1997 | Tovey et al. |
| 5,662,666 | A | 9/1997 | Onuki et al. |
| 5,674,229 | A | 10/1997 | Tovey et al. |
| 5,674,230 | A | 10/1997 | Tovey et al. |
| 5,681,331 | A | 10/1997 | de la Torre et al. |
| 5,690,652 | A | 11/1997 | Wurster et al. |
| 5,690,653 | A | 11/1997 | Richardson et al. |
| 5,702,408 | A | 12/1997 | Wales et al. |
| 5,709,692 | A | 1/1998 | Mollenauer et al. |
| 5,715,942 | A | 2/1998 | Li et al. |
| 5,725,557 | A | 3/1998 | Gatturna et al. |
| 5,728,107 | A | 3/1998 | Zlock et al. |
| 5,728,109 | A | 3/1998 | Schulze et al. |
| 5,728,113 | A | 3/1998 | Sherts |
| 5,730,747 | A | 3/1998 | Ek et al. |
| 5,746,751 | A | 5/1998 | Sherts |
| 5,749,898 | A | 5/1998 | Schulze et al. |
| 5,752,973 | A | 5/1998 | Kieturakis |
| 5,755,729 | A | 5/1998 | de la Torre et al. |
| 5,759,188 | A | 6/1998 | Yoon |
| 5,766,196 | A | 6/1998 | Griffiths |
| 5,779,646 | A | 7/1998 | Koblish et al. |
| 5,792,153 | A | 8/1998 | Swain et al. |
| 5,792,165 | A | 8/1998 | Klieman et al. |
| 5,797,537 | A | 8/1998 | Oberlin et al. |
| 5,797,927 | A | 8/1998 | Yoon |
| 5,797,928 | A | 8/1998 | Kogasaka |
| 5,814,051 | A | 9/1998 | Wenstrom, Jr. |
| 5,814,054 | A | 9/1998 | Kortenbach et al. |
| 5,814,069 | A | 9/1998 | Schulze et al. |
| 5,817,119 | A | 10/1998 | Klieman et al. |
| 5,827,323 | A | 10/1998 | Klieman et al. |
| 5,865,836 | A | 2/1999 | Miller |
| 5,871,488 | A | 2/1999 | Tovey et al. |
| 5,876,412 | A | 3/1999 | Piraka |
| 5,893,592 | A | 4/1999 | Schulze et al. |
| 5,897,563 | A | 4/1999 | Yoon et al. |
| 5,906,630 | A | 5/1999 | Anderhub et al. |
| 5,908,428 | A | 6/1999 | Scirica et al. |
| 5,911,727 | A | 6/1999 | Taylor |
| 5,928,136 | A | 7/1999 | Barry |
| 5,931,855 | A | 8/1999 | Buncke |
| 5,938,668 | A | 8/1999 | Scirica et al. |
| 5,941,430 | A | 8/1999 | Kuwabara |
| 5,947,982 | A | 9/1999 | Duran |
| 5,950,633 | A | 9/1999 | Lynch et al. |
| 5,954,731 | A | 9/1999 | Yoon |
| 5,954,733 | A | 9/1999 | Yoon |
| 5,957,937 | A | 9/1999 | Yoon |
| 5,980,538 | A | 11/1999 | Fuchs et al. |
| 5,984,932 | A | 11/1999 | Yoon |
| 5,993,466 | A | 11/1999 | Yoon |
| 5,993,467 | A | 11/1999 | Yoon |
| 5,997,565 | A | 12/1999 | Inoue |
| 6,004,332 | A | 12/1999 | Yoon et al. |
| 6,017,358 | A | 1/2000 | Yoon et al. |
| 6,027,522 | A | 2/2000 | Palmer |
| 6,051,006 | A | 4/2000 | Shluzas et al. |
| 6,071,289 | A | 6/2000 | Stefanchik et al. |
| 6,077,287 | A | 6/2000 | Taylor et al. |
| 6,080,180 | A | 6/2000 | Yoon |
| 6,086,601 | A | 7/2000 | Yoon |
| 6,119,913 | A | 9/2000 | Adams et al. |
| 6,126,665 | A | 10/2000 | Yoon |
| 6,126,666 | A | 10/2000 | Trapp et al. |
| 6,139,563 | A | 10/2000 | Cosgrove, III et al. |
| 6,143,005 | A | 11/2000 | Yoon et al. |
| 6,171,316 | B1 | 1/2001 | Kovac et al. |
| 6,206,893 | B1 | 3/2001 | Klein et al. |
| 6,214,028 | B1 | 4/2001 | Yoon et al. |
| 6,223,100 | B1 | 4/2001 | Green |
| 6,224,614 | B1 | 5/2001 | Yoon |
| 6,245,091 | B1 | 6/2001 | Buncke |
| 6,261,307 | B1 | 7/2001 | Yoon et al. |
| 6,277,132 | B1 | 8/2001 | Brhel |
| 6,319,262 | B1 | 11/2001 | Bates et al. |
| 6,332,889 | B1 | 12/2001 | Sancoff et al. |
| 6,346,111 | B1 | 2/2002 | Gordon et al. |
| 6,358,259 | B1 | 3/2002 | Swain et al. |
| 6,494,888 | B1 | 12/2002 | Laufer et al. |
| 6,506,196 | B1 | 1/2003 | Laufer |
| 6,517,539 | B1 | 2/2003 | Smith et al. |
| 6,533,796 | B1 | 3/2003 | Sauer et al. |
| 6,569,105 | B1 | 5/2003 | Kortenbach et al. |
| 6,582,450 | B2 | 6/2003 | Ouchi |
| 6,596,015 | B1 | 7/2003 | Pitt et al. |
| 6,599,310 | B2 | 7/2003 | Leung et al. |
| 6,638,287 | B2 | 10/2003 | Danitz et al. |
| 6,663,639 | B1 | 12/2003 | Laufer et al. |
| 6,663,641 | B1 | 12/2003 | Kovac et al. |
| 6,666,854 | B1 | 12/2003 | Lange |

(56) References Cited

U.S. PATENT DOCUMENTS

| | | |
|---|---|---|
| 6,676,676 B2 | 1/2004 | Danitz et al. |
| 6,719,764 B1 | 4/2004 | Gellman et al. |
| 6,719,765 B2 | 4/2004 | Bonutti |
| 6,743,239 B1 | 6/2004 | Kuehn et al. |
| 6,743,240 B2 | 6/2004 | Smith et al. |
| 6,755,843 B2 | 6/2004 | Chung et al. |
| 6,773,441 B1 | 8/2004 | Laufer et al. |
| 6,773,450 B2 | 8/2004 | Leung et al. |
| 6,786,913 B1 | 9/2004 | Sancoff et al. |
| 6,821,285 B2 | 11/2004 | Laufer et al. |
| 6,835,200 B2 | 12/2004 | Laufer et al. |
| 6,848,152 B2 | 2/2005 | Genova et al. |
| 6,889,116 B2 | 5/2005 | Jinno |
| 6,936,054 B2 | 8/2005 | Chu |
| 6,936,061 B2 | 8/2005 | Sasaki |
| 6,955,643 B2 | 10/2005 | Gellman et al. |
| 6,972,017 B2 | 12/2005 | Smith et al. |
| 6,981,628 B2 | 1/2006 | Wales |
| 6,991,635 B2 | 1/2006 | Takamoto et al. |
| 6,997,931 B2 | 2/2006 | Sauer et al. |
| 7,011,668 B2 | 3/2006 | Sancoff et al. |
| 7,037,315 B2 | 5/2006 | Sancoff et al. |
| 7,041,111 B2 | 5/2006 | Chu |
| 7,052,489 B2 | 5/2006 | Griego et al. |
| RE39,152 E | 6/2006 | Aust et al. |
| 7,056,331 B2 | 6/2006 | Kaplan et al. |
| 7,063,710 B2 | 6/2006 | Takamoto et al. |
| 7,063,715 B2 | 6/2006 | Onuki et al. |
| 7,107,124 B2 | 9/2006 | Green |
| 7,153,314 B2 | 12/2006 | Laufer et al. |
| 7,191,900 B2 | 3/2007 | Opie et al. |
| 7,192,437 B2 | 3/2007 | Shalaby |
| 7,211,093 B2 | 5/2007 | Sauer et al. |
| 7,218,972 B2 | 5/2007 | Rodriguez |
| 7,225,512 B2 | 6/2007 | Genova et al. |
| 7,226,468 B2 | 6/2007 | Ruff |
| 7,232,448 B2 | 6/2007 | Battles et al. |
| 7,244,260 B2 | 7/2007 | Koseki |
| 7,248,944 B2 | 7/2007 | Green |
| 7,351,250 B2 | 4/2008 | Zamierowski |
| 7,371,253 B2 | 5/2008 | Leung et al. |
| 7,413,571 B2 | 8/2008 | Zamierowski |
| 7,468,068 B2 | 12/2008 | Kolster |
| 7,601,164 B2 | 10/2009 | Wu |
| 7,645,284 B2 | 1/2010 | Burbank et al. |
| 7,666,194 B2 | 2/2010 | Field et al. |
| 7,691,112 B2 | 4/2010 | Chanduszko et al. |
| 7,704,261 B2 | 4/2010 | Sakamoto et al. |
| 7,708,747 B2 | 5/2010 | Bjerken |
| 7,722,630 B1 | 5/2010 | Stone et al. |
| 7,731,726 B2 | 6/2010 | Belhe et al. |
| 7,736,372 B2 | 6/2010 | Reydel et al. |
| 7,758,597 B1 | 7/2010 | Tran et al. |
| 7,758,598 B2 | 7/2010 | Conlon et al. |
| 7,766,925 B2 | 8/2010 | Stokes et al. |
| 7,771,438 B2 | 8/2010 | Dreyfuss et al. |
| 7,776,059 B2 | 8/2010 | Craig |
| 7,776,066 B2 | 8/2010 | Onuki et al. |
| 7,780,701 B1 | 8/2010 | Meridew et al. |
| 7,784,612 B2 | 8/2010 | Kanda et al. |
| 7,798,325 B2 | 9/2010 | Wizemann et al. |
| 7,814,630 B2 | 10/2010 | Price et al. |
| 7,815,654 B2 | 10/2010 | Chu |
| 7,815,659 B2 | 10/2010 | Conlon et al. |
| 7,828,812 B2 | 11/2010 | Stokes et al. |
| 7,833,235 B2 | 11/2010 | Chu |
| 7,833,237 B2 | 11/2010 | Sauer |
| 7,837,696 B2 | 11/2010 | Modesitt et al. |
| 7,842,047 B2 | 11/2010 | Modesitt et al. |
| 7,842,048 B2 | 11/2010 | Ma |
| 7,846,170 B2 | 12/2010 | Modesitt et al. |
| 7,850,701 B2 | 12/2010 | Modesitt et al. |
| 7,883,517 B2 | 2/2011 | Pantages et al. |
| 7,883,519 B2 | 2/2011 | Oren et al. |
| 7,887,554 B2 | 2/2011 | Stokes et al. |
| 7,935,128 B2 | 5/2011 | Rioux et al. |
| 7,947,052 B2 | 5/2011 | Baxter, III et al. |
| 7,947,053 B2 | 5/2011 | McKay et al. |
| 7,951,157 B2 | 5/2011 | Gambale |
| 7,967,832 B2 | 6/2011 | Chu |
| 7,967,842 B2 | 6/2011 | Bakos |
| 7,972,344 B2 | 7/2011 | Murray et al. |
| 7,976,552 B2 | 7/2011 | Suzuki |
| 2002/0010480 A1 | 1/2002 | Sancoff et al. |
| 2002/0065526 A1 | 5/2002 | Oren et al. |
| 2002/0072702 A1 | 6/2002 | Quay |
| 2002/0128666 A1 | 9/2002 | Sancoff et al. |
| 2002/0173800 A1 | 11/2002 | Dreyfuss et al. |
| 2002/0198542 A1 | 12/2002 | Yamamoto et al. |
| 2003/0009195 A1 | 1/2003 | Field et al. |
| 2003/0014077 A1 | 1/2003 | Leung et al. |
| 2003/0045891 A1 | 3/2003 | Yamamoto et al. |
| 2003/0105475 A1 | 6/2003 | Sancoff et al. |
| 2003/0105476 A1 | 6/2003 | Sancoff et al. |
| 2003/0114863 A1 | 6/2003 | Field et al. |
| 2003/0116670 A1 | 6/2003 | Gentry |
| 2003/0171761 A1 | 9/2003 | Sancoff et al. |
| 2003/0233104 A1 | 12/2003 | Gellman et al. |
| 2004/0010245 A1 | 1/2004 | Cerier et al. |
| 2004/0060410 A1 | 4/2004 | Leung et al. |
| 2004/0068272 A1 | 4/2004 | Sauer et al. |
| 2004/0087976 A1 | 5/2004 | DeVries et al. |
| 2004/0092967 A1 | 5/2004 | Sancoff et al. |
| 2004/0181243 A1 | 9/2004 | Chu et al. |
| 2004/0193186 A1 | 9/2004 | Kortenbach et al. |
| 2004/0199184 A1 | 10/2004 | Topper et al. |
| 2004/0249394 A1 | 12/2004 | Morris et al. |
| 2004/0260314 A1 | 12/2004 | Lizardi et al. |
| 2005/0043747 A1 | 2/2005 | Field et al. |
| 2005/0085832 A1 | 4/2005 | Sancoff et al. |
| 2005/0096694 A1 | 5/2005 | Lee |
| 2005/0126876 A1 | 6/2005 | Simmons |
| 2005/0165419 A1 | 7/2005 | Sauer et al. |
| 2005/0256533 A1 | 11/2005 | Roth et al. |
| 2005/0288690 A1 | 12/2005 | Bourque et al. |
| 2006/0025817 A1 | 2/2006 | Ortiz et al. |
| 2006/0036232 A1 | 2/2006 | Primavera et al. |
| 2006/0069396 A1 | 3/2006 | Meade et al. |
| 2006/0111209 A1 | 5/2006 | Hinman et al. |
| 2006/0235304 A1 | 10/2006 | Harhen et al. |
| 2006/0253126 A1 | 11/2006 | Bjerken et al. |
| 2006/0282093 A1 | 12/2006 | Shelton, IV et al. |
| 2007/0005110 A1 | 1/2007 | Collier et al. |
| 2008/0188868 A1 | 8/2008 | Weitzner et al. |
| 2008/0312688 A1* | 12/2008 | Nawrocki et al. ............ 606/228 |

FOREIGN PATENT DOCUMENTS

| | | |
|---|---|---|
| EP | 0647431 A | 4/1995 |
| EP | 1 481 628 A1 | 12/2004 |
| EP | 1 915 957 A2 | 4/2008 |
| EP | 1 915 966 A1 | 4/2008 |
| EP | 2 044 890 A1 | 4/2009 |
| WO | WO 98/11814 A2 | 3/1998 |
| WO | WO 98/11829 A1 | 3/1998 |
| WO | WO 98/53745 A1 | 12/1998 |
| WO | WO 99/15090 A1 | 4/1999 |
| WO | WO 99/18859 A1 | 4/1999 |
| WO | WO 00/67834 A1 | 11/2000 |
| WO | WO01/74254 A | 10/2001 |
| WO | WO 02/34147 A1 | 5/2002 |
| WO | WO03/017850 A | 3/2003 |
| WO | WO2006/061868 A | 6/2006 |
| WO | WO 2008/042423 A2 | 4/2008 |
| WO | WO 2008/045333 A | 4/2008 |

(56) References Cited

FOREIGN PATENT DOCUMENTS

OTHER PUBLICATIONS

International Search Report for PCT/US2007/021506 mailed Apr. 16, 2008 (2 pgs.).

European Search Report for EP 07839357.6 date of completion Oct. 31, 2012 (10 pgs.).
European Search Report for EP 09251544.4 mailed Feb. 28, 2013 (18 pgs.).
European Search Report for EP 123169361.8-2310 date of completion is Jul. 24, 2012 (9 pages).

* cited by examiner

DEPLOYMENT SYSTEM FOR SURGICAL SUTURE

CROSS-REFERENCE TO RELATED APPLICATION

The present application claims the benefit of and priority to U.S. Provisional Application Ser. No. 61/123,900, filed on Apr. 11, 2008, the entire content of which is incorporated herein by reference.

The present application also claims the benefit of and priority to International Application Serial No. PCT/US07/21482, filed on Oct. 4, 2007, International Application Serial No. PCT/US07/21412, filed on Oct. 5, 2007, International Application Serial No. PCT/US07/21447, filed on Oct. 5, 2007, International Application Serial No. PCT/US07/21449, filed on Oct. 5, 2007, International Application Serial No. PCT/US07/21457, filed on Oct. 5, 2007, International Application Serial No. PCT/US07/21466, filed on Oct. 5, 2007, International Application Serial No. PCT/US07/21495, filed on Oct. 5, 2007, International Application Serial No. PCT/US07/21496, filed on Oct. 5, 2007, International Application Serial No. PCT/US07/21506, filed on Oct. 5, 2007, the entire content of each of which being incorporated herein by reference.

BACKGROUND

1. Technical Field

The present disclosure relates to a deployment system for insertion of a surgical suture into the body of a patient. More particularly, the present disclosure relates to a deployment system for use in inserting a length of a relatively stiff suture into the body of a patient laparoscopically.

2. Background of Related Art

Various surgical procedures often require the use of relatively stiff sutures to repair or reconnect tough tissues. Stiff sutures may be required in open surgical procedures where ligaments or tendons are being reconnected or may be required in endoscopic and/or laparoscopic surgical procedures where the stiff suture is required to be passed down through a narrow cannula along with an associated surgical instrument.

Attachment of the stiff sutures directly to a surgical needle may limit the ability to manipulate the surgical needle through the tough tissues without risk of tearing the tissues with the stiff suture or damaging the stiff suture itself by excessive bending of the suture. Further, direct attachment of the surgical needle to the stiff suture may limit the ability to advance the surgical needle and stiff suture through cannula structure to access the interior of a body cavity.

Therefore, it is desirable to provide a system for inserting a surgical needle and a stiff suture through tissues without risk of damage to the tissues and bending of the stiff suture. It would further be desirable to provide a system for deploying a surgical needle and a stiff suture through a cannula to dispose the surgical needle and stiff suture within a body cavity without risk of bending or breaking the suture.

SUMMARY

The present disclosure relates to a deployment system for use in inserting a length of a relatively stiff suture into the body of a patient laparoscopically.

According to one aspect of the present disclosure, a suture deployment system is provided and includes a surgical needle; a flexible suture having a distal end and a proximal end, the distal end of the flexible suture being attached to the surgical needle; and a target suture having a distal end and a proximal end, wherein the distal end of the target suture is secured to the proximal end of the flexible suture.

The target suture may include a plurality of barbs located on an outer surface of the target suture.

The suture deployment system may include a hollow collar having a distal end and a proximal end, the hollow collar being positioned intermediate the proximal end of the flexible suture and the distal end of the target suture. The distal end of the target suture may be releasably secured within the proximal end of the hollow collar. The target suture may be a monofilament. The target suture may be releasably secured to the proximal end of the flexible suture.

The distal end of the flexible suture may be secured within a suture hole formed in a body portion of the surgical needle. The suture hole may be formed in a center of the body portion. The distal end of the flexible suture may be crimped within the suture hole formed in the body portion. The surgical needle may be a double pointed needle having a tissue penetrating tip formed at each end of the body portion. The surgical needle may include engagement slots formed adjacent each tissue penetrating tip for receipt of engagement structure associated with a surgical suturing apparatus.

According to another aspect of the present disclosure, a suture deployment system includes a surgical needle having a body portion and a tissue penetrating tip formed at each end of the body portion; a multifilament suture having a distal end and a proximal end, the distal end of the multifilament suture being secured within the suture hole in the body portion of the surgical needle; a hollow collar having a distal end and a proximal end, the proximal end of the multifilament suture being within the distal end of the hollow collar; and a monofilament target suture having a distal end and a proximal end, wherein the distal end of the monofilament target suture is releasably secured within the proximal end of the hollow collar.

The monofilament target suture may be a barbed suture.

The surgical needle may include at least one crimping bump adjacent the suture hole.

The surgical needle may include at least one engagement slot for receipt of engagement structure associated with a surgical suturing apparatus.

The barb suture may be a compound barb suture including an elongated body; and at least one barb extending from the elongated body and defining an inner surface. The inner surface may include a first portion disposed at a first orientation relative to a longitudinal axis of the elongated body; and a second portion disposed at a second orientation relative to the longitudinal axis. At least one of the first and second portions may be substantially linear.

The first and second portions may be at first and second angles relative to respective longitudinal axes of the elongated body. The second angle may be less than the first angle. The first angle may be between about 0 degrees to about 90 degrees. The first angle may be between about 30 degrees to about 50 degrees. The second angle may be between about 0 degrees to about 90 degrees. The second angle may be between about 2 degrees to about 25 degrees.

The inner surface of the at least one barb may include a third portion disposed at a third orientation relative to the longitudinal axis of the elongated body, wherein the third orientation defines a third angle that is between about 0 degrees to about 90 degrees. The third angle may be between about 2 degrees to about 50 degrees.

There is also disclosed a suture deployment system including a surgical needle and a flexible suture having a distal end and a proximal end. The distal end of the flexible suture is fixedly secured to the surgical needle. A target suture is provided and has a distal end and a proximal end. The distal end of the target suture is releasably secured to the proximal end of the flexible suture. A hollow collar, having a distal end and a proximal end, is positioned intermediate the proximal end of the flexible suture and the distal end of the target suture. The distal end of the target suture is releasably secured within the proximal end of the hollow collar.

In one embodiment, the target suture is a relatively stiff suture. In a specific embodiment, the target suture includes a plurality of barbs located on an outer surface of the target suture.

The distal end of the flexible suture is secured within a suture hole formed in a body portion of the surgical needle. The suture hole is formed in a center of the body portion. The distal end of the flexible suture is crimped within the suture hole formed in the body portion.

In one embodiment, the surgical needle is a double pointed needle having a tissue penetrating tip formed at each end of the body portion. In a more specific embodiment, the surgical needle includes engagement slots formed adjacent each tissue penetrating tip for receipt of engagement structure associated with a surgical suturing apparatus.

There is also disclosed a suture deployment system including a surgical needle having a body portion and a tissue penetrating tip formed at each end of the body portion. The surgical needle includes a suture hole located centrally within the body portion. The suture deployment system also includes a flexible, multifilament suture having a distal end and a proximal end, the distal end of the multifilament suture being secured within the suture hole in the body portion of the surgical needle. The suture deployment system further includes a hollow collar having a distal end and a proximal end, the proximal end of the multifilament suture being fixedly secured within the distal end of the hollow collar. The suture deployment system additionally includes a relatively stiff target suture having a distal end and a proximal end. The distal end of the stiff target suture is releasably secured within the proximal end of the hollow collar.

In a specific embodiment, the relatively stiff target suture is a barbed suture. In another specific embodiment, the surgical needle includes at least one crimping bump adjacent the suture hole. In yet a more specific embodiment, the surgical needle includes at least one engagement slot for receipt of engagement structure associated with a surgical suturing apparatus.

DESCRIPTION OF THE DRAWINGS

An embodiment of the presently disclosed suture deployment system is disclosed herein with reference to the drawings, wherein.

DETAILED DESCRIPTION OF EMBODIMENTS

An embodiment of the presently disclosed suture deployment system will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component further away from the user.

Figures 1, 2:
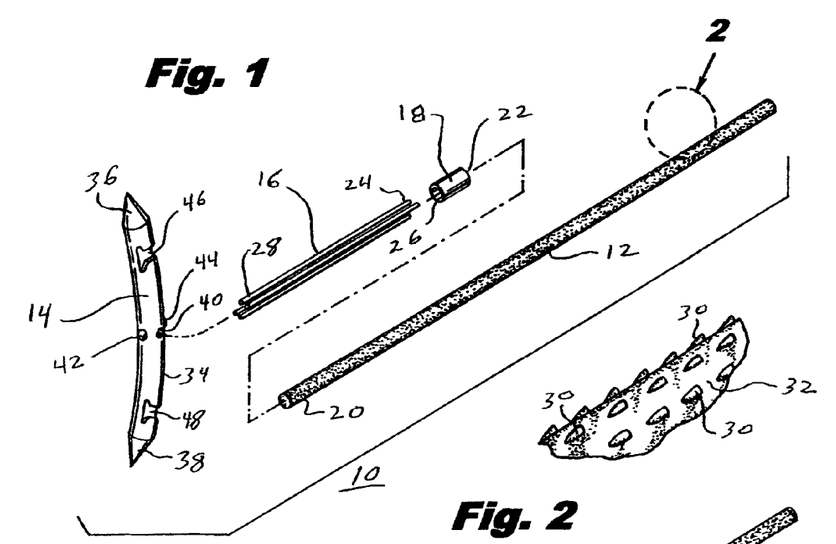
FIG. 1 is a perspective view of a suture deployment system with parts separated.
FIG. 2 is an enlarged area of detail view of FIG. 1.

Referring to FIG. 1, there is disclosed a suture deployment system 10 for use in carrying, and manipulating, a relatively stiff target suture 12 of suture deployment system 10 into the body of a patient. Suture deployment system 10 generally includes target suture 12 and a surgical needle 14 for piercing tissue so as to position target suture 12 therethrough. A relatively flexible suture 16 is positioned between surgical needle 14 and target suture 12 and allows surgical needle 14 to be manipulated within a body cavity and through tissue without causing undue bending of target suture 16 as described in more detail below. Additionally, flexible suture 16 enables target suture 12 to be connected to surgical needle 14 and inserted through a cannula without danger of bending or breaking target suture 12. A hollow ferrule or collar 18 is provided to releasably connect flexible suture 16 to target suture 12 and allow target suture 12 to remain in tissue after the remainder of suture deployment system 10 is removed from the body of the patient.

Specifically, a distal end 20 of target suture 12 is releasably held within a proximal end 22 of collar 18. A proximal end 24 of flexible suture 16 is fixedly secured within a distal end 26 of collar 18. Likewise, a distal end 28 of flexible suture 16 is fixedly secured to surgical needle 14 in a manner described in more detail below.

Referring for the moment to FIG. 2, target suture 12 is a stiff suture of the type used in connection with the repair of relatively tough tissues where suture strength and not bending or wrapping of the suture material is most important. Examples of such applications may include, for example, ligament or tendon repair and reconnection, etc. Target suture 12 may be a "barbed suture" having a series of anchoring projections or barbs 30 formed on an outer surface 32 thereof. Barbs 30 facilitate anchoring target suture 12 within the relatively tough tissues.

Referring back to FIG. 1, in contrast to target suture 12, flexible suture 16 is relatively flacid which allows surgical needle 14 to be manipulated without putting bending stresses on target suture 12. In one embodiment, flexible suture 16 is a relatively short length of multifilament suture of a type typically known in the art. As noted above, collar 18 is provided to releasably connect target suture 12 to flexible suture 16. Collar 18 may be formed from a variety of biocompatible materials, such as, for example, polymeric materials, stainless steel, etc.

Sutures of the present disclosure may be absorbable or non-absorbable. It should be understood that combinations of filaments made from different materials (e.g. natural and synthetic, or bioabsorbable and non-bioabsorbable materials) may be used to make the present sutures.

Suitable synthetic absorbable materials include polymers such as those made from lactide, glycolide, caprolactone, valerolactone, carbonates (e.g., trimethylene carbonate, tetramethylene carbonate), dioxanones (e.g., 1,4-dioxanone) δ-valerolactone, 1,dioxepanones (e.g., 1,4-dioxepan-2-one and 1,5-dioxepan-2-one), ethylene glycol, ethylene oxide, esteramides, γ-hydroxyvalerate, β-hydroxypropionate, alpha-hydroxy acid, hydroxybuterates, orthoesters, hydroxy alkanoates, tyrosine carbonates, polyimide carbonates, polyimino carbonates such as poly (bisphenol A-iminocarbonate) and poly (hydroquinone-iminocarbonate), and polymer drugs (e.g., polydiflunisol, polyaspirin, and protein therapeutics) and copolymers and combinations thereof. Suitable natural absorbable polymers include collagen, cellulose and gut. In embodiments, glycolide and lactide based polyesters, including copolymers of lactide and glycolide may be used.

Suitable non-absorbable materials which may be used to form the sutures disclosed herein include non-absorbable natural materials such as cotton, silk, and rubber. Suitable non-absorbable synthetic materials include monomers and polymers derived from materials such as nylons, polyolefins such as polypropylene and polyethylene, ultra high molecular weight polyethylene (UHMWPE), polyamides, polyesters such as poly butylene terephthalate (PBT), poly trimethylene terephthalate (PTT), poly ethylene terephthalate (PET), polyaryletherketone, polyvinylidene difluoride (PVDF), acrylic, polyamides, aramids, fluropolymers, polybutesters, silicones, and polymer blends, copolymers thereof and combinations with degradable polymers. Polypropylene can also be utilized to form the suture. The polypropylene can be isotactic polypropylene or a mixture of isotactic and syndiotactic or atactic polypropylene. Additionally, non-absorbable synthetic and natural polymers and monomers may be combined with each other and may also be combined with various absorbable polymers and monomers to create fibers and filaments for the present sutures.

As used herein, the terms "fibers", "filaments" and "yarns" each may be used to construct the sutures in whole or in part. The term "fibers," in this context, are generally used to designate natural or synthetic structures that have a length approximately 3 orders of magnitude greater than their diameter or width. The term "filaments" are typically used to describe "fibers" of indefinite or extreme length, and "yarns" as a generic term for a continuous strand of twisted or untwisted "fibers" or "filaments" in a form suitable for knitting, weaving, braiding or otherwise intertwining.

Flexible sutures 16 of the present disclosure may be multifilament (e.g. braided) and target sutures 12 may be monofilamant. Methods for making sutures from these suitable materials are within the purview of those skilled in the art (e.g. extrusion and molding). The filaments may be combined to create a multifilament suture using any technique within the purview of one skilled in the art such as commingling, twisting, braiding, weaving, entangling, and knitting. For example, filaments may simply be combined to form a yarn or they may be braided. In another example, filaments may be combined to form a yarn and then those multifilament yarns may be braided. Those skilled in the art reading this disclosure will envision other ways in which filaments may be combined. Fibers may also be combined to produce a nonwoven multifilament large diameter suture. In certain embodiments, a multifilament structure useful in forming an anchoring suture according to the present disclosure may be produced by braiding. The braiding can be done by any method within the purview of those skilled in the art. Furthermore, the anchoring suture may include portions which are monofilament and portions which are multifilament. In some embodiments, the proximal end of the elongate body may be a multifilament and the looped portion (loop portion described below) may be a monofilament.

In certain embodiments, the sutures in whole or in part (e.g. anchors) may be constructed using shape memory polymers. Suitable polymers used to prepare hard and soft segments of shape memory polymers include polycaprolactone, dioxanone, lactide, glycolide, polyacrylates, polyamides, polysiloxanes, polyurethanes, polyether amides, polyurethane/ureas, polyether esters, and urethane/butadiene copolymers and combinations thereof.

In some embodiments, the sutures may include metals (e.g. steel and degradable magnesium), metal alloys or the like.

Additionally, the sutures may include biologically acceptable additives such as plasticizers, antioxidants, dyes, dilutants, bioactive agents and combinations thereof, which can be coated on the filaments or fibers, or impregnated into the fibers or filaments (e.g. during compounding or extrusion) used to form the suture of the present disclosure.

Various compositions and materials may also be applied to the sutures or included in the filaments or fibers to improve mechanical properties such as handling and knot strength or to deliver medicinal agents. Suitable coating materials include any materials conventionally applied to sutures. For example, suitable materials include fatty acid esters which may be combined with the metal salt of a fatty acid in the coating composition. Such esters include, for example, calcium stearate, stearoyl lactylate esters, palmityl lactylate esters, oleyl lactylate esters such as calcium, magnesium, aluminum, barium, or zinc stearoyl lactylate, calcium, magnesium, aluminum, barium, or zinc palmityl lactylate; calcium, magnesium, aluminum, barium, or zinc oleyl lactylate; with calcium stearate and calcium stearoyl-2-lactylate (such as the calcium stearoyl-2-lactylate commercially available under the trade name VERV from American Ingredients Co., Kansas City, Mo.) being preferred. When desirable, the fatty acid ester may be combined with a solvent. Suitable solvents include polar and non-polar solvents including but not limited to alcohols (e.g., methanol, ethanol, propanol), chlorinated hydrocarbons (such as methylene chloride, chloroform, 1,2-dichloro-ethane), and aliphatic hydrocarbons such as hexane, heptene, ethyl acetate.

In embodiments, the sutures may be combined with and/or coated with suitable materials including polyalkylene oxides such as polyethylene oxide, polypropylene oxide, polyethylene glycol (PEG), polypropylene glycol, copolymers thereof, and the like, including those having acrylate groups such as acrylate PEGs, and acrylate PEG/PPG copolymers. Such combinations may include blends or copolymers with polyalkylene oxide oligomers or polymers or other non-toxic surfactants. The resulting composition may possess antimicrobial properties due to the presence of the copolymers described above. In other embodiments, the sutures may be combined with silicone acrylates. Coatings may be applied to the individual filaments or to the entire suture at any time prior to sterilization techniques. Coatings can be applied to the filaments using any technique within the purview of those skilled in the art.

Additionally, the sutures may incorporate various pharmaceuticals and medicinal agents. Medicinal agents and drugs may be applied to the sutures and/or construct materials by methods within the purview of those skilled in the art, including but not limited to dipping, spraying, brushing, vapor deposition, coextrusion, capillary wicking, film casting, molding and the like. Additionally, solvents may be used to incorporate various agents into the anchoring suture. Suitable solvent include those listed above.

Medicinal agents which may be incorporated into the sutures include antimicrobial agents, anti-virals, anti-fungals, and the like. Antimicrobial agents as used herein is defined by an agent which by itself or through assisting the body (immune system) helps the body destroy or resist microorganisms which may be pathogenic (disease causing). The term "antimicrobial agent" includes antibiotics, quorum sensing blockers, surfactants, metal ions, antimicrobial proteins and peptides, antimicrobial polysaccharides, antiseptics, disinfectants, anti-virals, anti-fungals, and combinations thereof.

Agents may be incorporated into a coating using solvents or mixed with various monomers or polymers and applied to anchoring suture. Additional suitable medicinal agents which may be used include colorants, dyes, preservatives, protein and peptide preparations, protein therapeutics, polysaccharides such as hyaluronic acid, lectins, lipids, probiotics, antibiotics, angiogenic agents, anti-thrombotics, anti-clotting agents, clotting agents, analgesics, anesthetics, wound repair agents, chemotherapeutics, biologics, anti-inflammatory agents, anti-proliferatives, diagnostic agents, antipyretic, antiphlogistic and analgesic agents, vasodilators, antihypertensive and antiarrhythmic agents, hypotensive agents, antitussive agents, antineoplastics, local anesthetics, hormone preparations, antiasthmatic and antiallergic agents, antihistaminics, anticoagulants, antispasmodics, cerebral circulation and metabolism improvers, antidepressant and antianxiety agents, vitamin D preparations, hypoglycemic agents, antiulcer agents, hypnotics, antibiotics, antifungal agents, sedative agents, bronchodilator agents, antiviral agents, dysuric agents, brominated or halogenated furanones, and the like. In embodiments, polymer drugs, i.e., polymeric forms of such compounds for example, polymeric antibiotics, polymeric antiseptics, polymeric chemotherapeutics, polymeric anti-proliferatives, polymeric antiseptics, polymeric non-steroidal anti-inflammatory drugs (NSAIDS), and the like may be utilized and combinations thereof.

The sutures of the present disclosure can additionally contain suitable medicinal agents such as viruses and cells, peptides, polypeptides and proteins, analogs, muteins, and active fragments thereof, such as immunoglobulins, antibodies (monoclonal and polyclonal), cytokines (e.g. lymphokines, monokines, chemokines), blood clotting factors, hemopoietic factors, interleukins (IL-2, IL-3, IL-4, IL-6), interferons (β-IFN, α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.) hormones and hormone analogs (e.g., growth hormone), vaccines (e.g., tumoral, bacterial and viral antigens), somatostatin, antigens, blood coagulation factors, growth factors, protein inhibitors, protein antagonists, and protein agonists, nucleic acids, such as antisense molecules, DNA, RNA, oligonucleotides, polynucleotides and ribozymes and combinations thereof.

Methods for combining these medicinal agents with compositions of the present disclosure are within the purview of those skilled in the art and include, but are not limited to mixing, blending, dipping, spraying, wicking, solvent evaporating and the like.

As mentioned above and as seen in FIG. 2, target suture 12 may be a "barbed suture" having a series of anchoring projections or barbs 30 formed on an outer surface 32 thereof. Barbs 30 facilitate anchoring target suture 12 within the relatively tough tissues.

The barbs can be arranged in any suitable pattern along a length thereof including helical, linear, or randomly spaced with respect to longitudinal axis "A". The number, configuration, spacing and surface area of the barbs can vary depending upon the tissue in which the suture is used, as well as the composition and geometry of the material utilized to form the suture. For example, if the wound closure device is intended to be used in fatty tissue, which is relatively soft, the barbs may be longer and spaced further apart to enable to suture to grip the soft tissue. The barbs can be arranged in various directions at various angles or a single barb may include more than one angle, such as a compound barb.

Figure 2A:
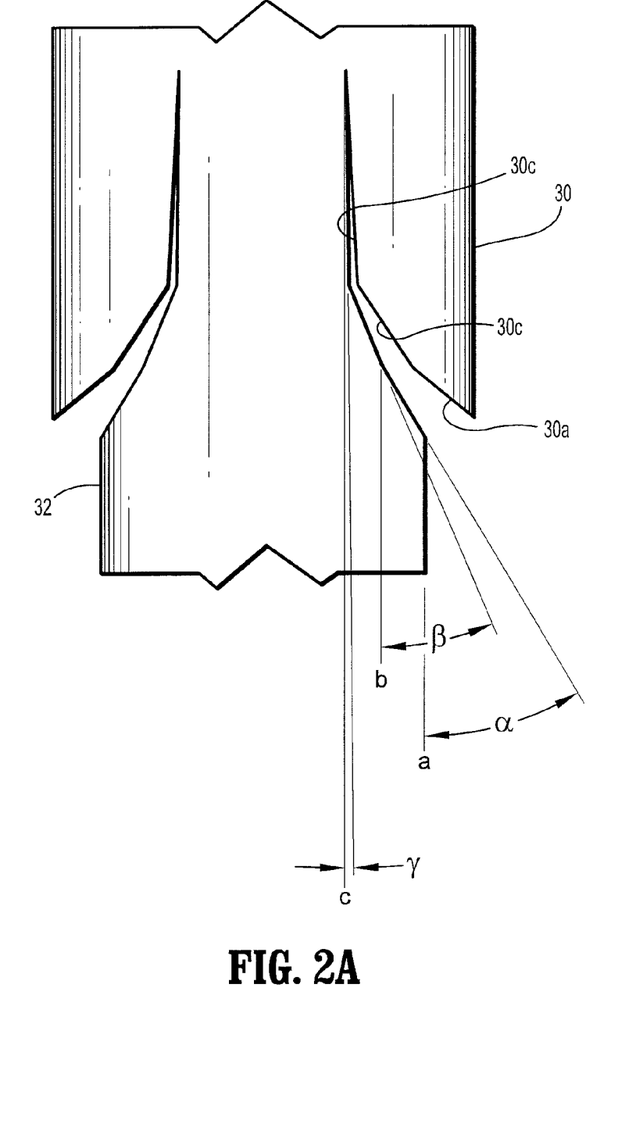
FIG. 2A is a plan view of a segment of a barbed suture of the suture deployment system of FIG. 1.

In an alternate embodiment, as seen in FIG. 2A, the sutures may include a compound barb having an inner surface including a first angle, disposed at a first orientation relative to a longitudinal axis "A" thereof and a second angle having a second inner surface, disposed at a second orientation relative to a longitudinal axis "B" thereof.

As seen in FIG. 2A, compound barbs 30 having first, second and third portions 12a-c are generally formed by cutting into the surface of elongated body 14. In embodiments, each of the first, second, and third portions 12a-c may be cut at first, second and third angles $\alpha$, $\beta$, and $\gamma$ relative to longitudinal axes a, b, and c respectively of elongated body 14 which are parallel to a central longitudinal axis 'D', wherein the second angle $\beta$ is less than the first angle $\alpha$, and the third angle $\gamma$ is less than the second angle $\beta$. Compound barb 12 may include a first portion 12a which is formed by cutting into elongated body 14 at a first angle $\alpha$ of from about 0 degrees to about 90 degrees relative to longitudinal axis "a", in other embodiments, the first angle $\alpha$ ranges from about 30 degrees to about 50 degrees relative to longitudinal axis "a", a second portion 12b which is formed by cutting into elongated body 14 at a second angle $\beta$ of from about 0 degrees to about 90 degrees relative to the longitudinal axis "b", in other embodiments, the second angle $\beta$ ranges from about 2 degrees to about 25 degrees relative to the longitudinal axis "b", and optionally a third portion 12c which is formed by cutting into elongated body 14 at a third angle $\gamma$ of from about 0 degrees to about 90 degrees relative to longitudinal axis "c", in other embodiments, the third angle $\gamma$ ranges from about 2 degrees to about 50 degrees relative to longitudinal axis "c". Reference may be made to U.S. Provisional Application Ser. No. 61/029,964, filed on Feb. 20, 2008, entitled "Compound Barb Medical Device and Method," the entire content of which is incorporated herein by reference, for a detailed discussion of various geometries of compound barbs and the like.

The suture may optionally include a third orientation different from the first and second orientation. In an embodiment, the first, second and third orientations are each disposed at different angles with respect to the longitudinal axis. In some embodiments, the suture may include a staggered arrangement of large or small barbs. In other embodiments, the sutures may have a random configuration of both large and small barbs.

The surface area of the plurality of barbs can also vary. For example, fuller-tipped barbs can be made of varying sizes designed for specific surgical applications. When joining fat and relatively soft tissues, larger barbs may be desired, whereas smaller barbs may be more suitable for collagen-dense tissues. In some embodiments, a combination of large and small barbs within the same structure may be beneficial, for example when a fiber is used in tissue repair with differing layer structures. Use of the combination of large and small anchors with the same fiber wherein barb sizes are customized for each tissue layer will ensure maximum holding properties.

Surgical needle 14 is provided to pierce tissue and draw flexible suture 16 and target suture 12 through relatively tough tissue. Surgical needle 14 takes the form of any of the various known surgical needles used for carrying and threading suture material through tissue. In the disclosed embodiment, surgical needle 14 is double pointed needle specifically configured for use with a surgical suturing apparatus (described below) capable of driving surgical needle 14 through tough tissue. Surgical needle 14 generally includes a curved body portion 34 having first and second end points 36 and 38, respectively. Body portion 34 includes a central suture hole 44 for receipt of distal end 28 of flexible suture 16. A pair of crimping bumps 42 and 44 are provided adjacent suture hole 40 for securing flexible suture 16 within suture hole 40 as described in more detail hereinbelow. Engagement slots 46 and 48 are provided adjacent pointed ends 36 and 38. Engagement slots 46 and 48 are configured to alternately receive engagement structure associated with the surgical suturing apparatus, described hereinbelow, in order to pass surgical needle 14 back-and-forth between jaws of the surgical suturing apparatus. Exemplary of embodiments of surgical needle 14 are disclosed in U.S. Pat. No. 5,569,301 to Granger et al., the entire disclosure of which is incorporated by reference herein.

Figure 3:
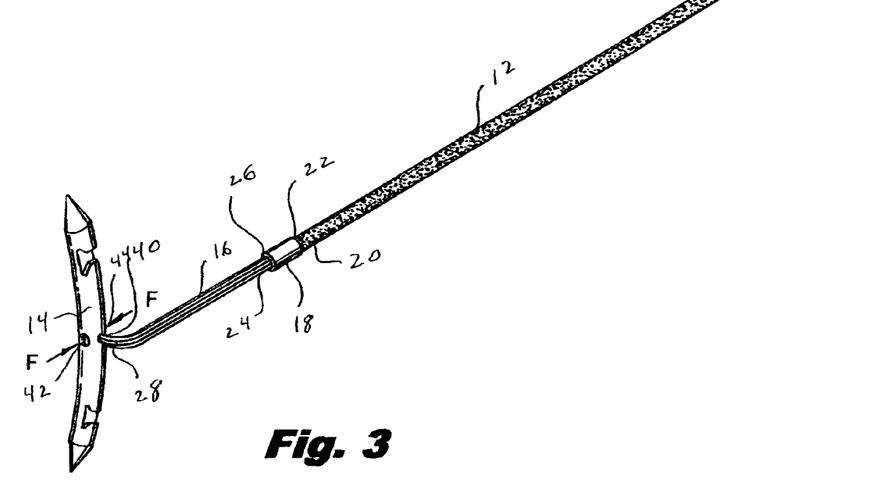
FIG. 3 is a perspective view of the assembled suture deployment system of FIG. 1.

Referring now to FIGS. 1 and 3, in order to assemble suture deployment system 10, proximal end 24 of flexible suture 16 is inserted within distal end 26 of collar 18 and fixedly secured therein by various known methods, such as, for example, gluing, welding, crimping, etc. Distal end 20 of target suture 12 is inserted within proximal end 22 of collar 18 and secured therein in a manner which will allow distal end 20 to separate from collar 18 upon the application of sufficient force to collar 18. This may be accomplished by utilizing weak adhesives, partial crimping of collar 18 about distal end 20 of target suture 12, or simply a friction fit of distal end 20 within proximal end 22 of collar 18. It should be noted that the securement of distal end 26 of collar 18 about proximal end 24 of flexible suture 16 is substantially stronger than the securement of distal end 20 of target suture 12 within proximal end 22 of collar 18. Thus, upon the application of sufficient tension on flexible suture 16, flexible suture 16 will remain attached to collar 18 while target suture 12 releasably detaches from collar 18.

In order to secure distal end 28 of flexible suture 16 to surgical needle 14, distal end 28 is inserted in suture hole 40 formed in body portion 34 of surgical needle 14. Thereafter, a crimping force is applied in the directions of arrows F to compress or crimp bumps 42 and 44 causing suture hole 40 to close or crimp about distal end 28 of flexible suture 16 (see U.S. Pat. No. 5,569,301 to Granger et al.).

While a collar 18 has been described and illustrated for connecting target suture 12 and flexible suture 16 to one aonther, other methods are contemplated and included in the present disclosure, including and not limited to the use of an overmold extending over and between target suture 12 and flexible suture 16, the fusing of target suture 12 and flexible suture 16 to one another, and the like.

Figure 4:
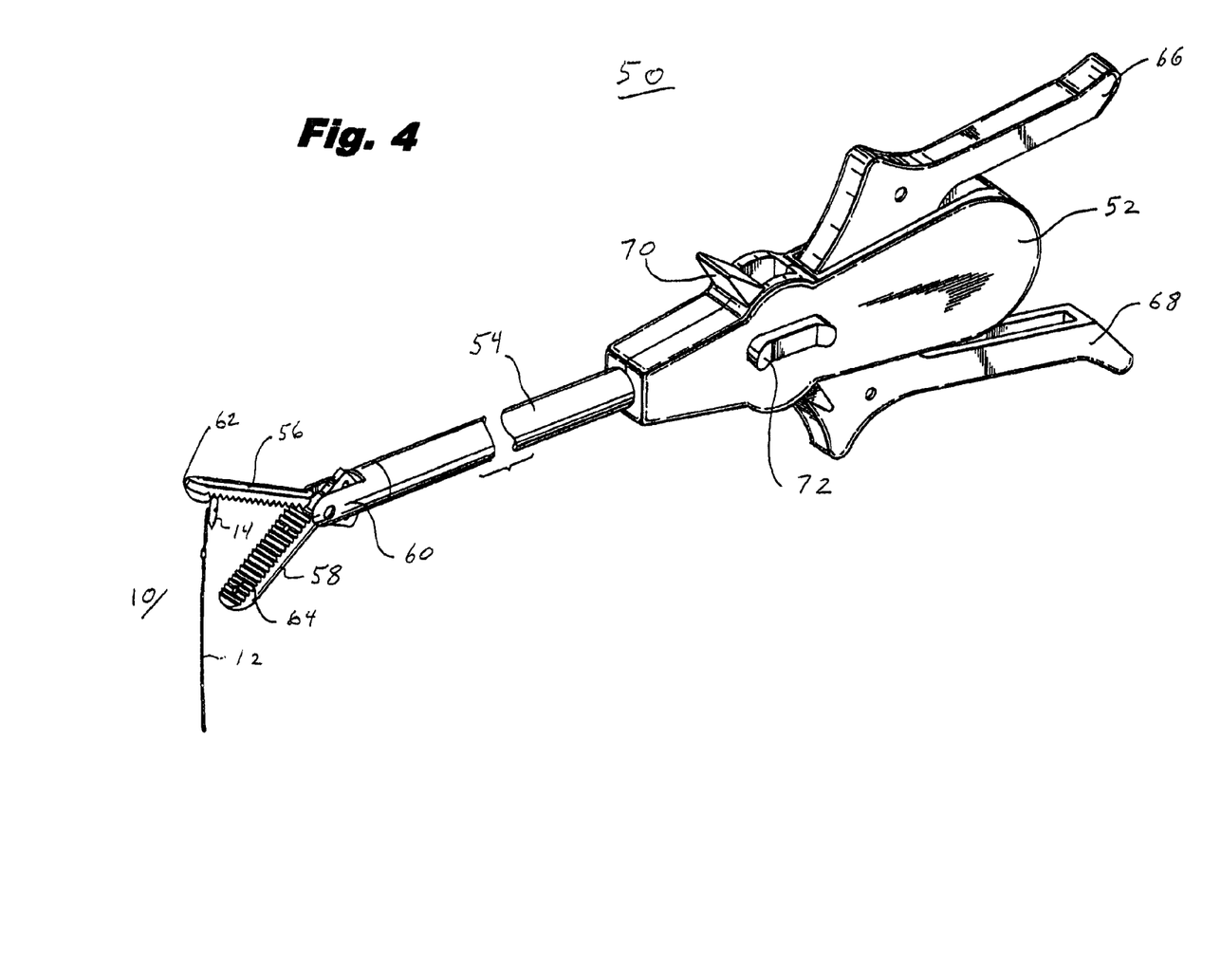
FIG. 4 is a perspective view of the suture deployment system of FIG. 1 and a surgical suturing apparatus for use with the suture deployment system.

Referring now to FIG. 4, there is illustrated a surgical suturing apparatus 50 for use in transporting suture deployment system 10 through a cannula and manipulating surgical needle 13 through tissue. Surgical suturing apparatus 50 generally includes a body portion 52 having an elongate tubular member 54 extending distally from body portion 52. First and second jaws 56 and 58 are movably mounted on a distal end 60 of elongate tubular member 54. A pair of handles 66 and 68 are movably mounted on body portion 52 and are operable to move first and second jaws 56 and 58 between an open position substantially spaced apart to a closed position wherein first and second jaws 56 and 58 are substantially adjacent each other. First and second jaws 56 and 58 are provided to alternately engage surgical needle 14 and pass surgical needle 14 through tissue. Specifically, first and second jaws 56 and 58 include first and second needle receiving holes 62 and 64, respectively, for receipt of surgical needle 14. A toggle lever 70 is provided on body portion 52 and operates to alternately secure surgical needle 14 within needle holes 62 and 64 of first and second jaws 56 and 58, respectively. Engagement structure (not shown) is associated with toggle lever 70 and functions to alternately engage slots 46 and 48 in surgical needle 14 to alternately secure surgical needle 14 in first and second jaws 56 and 58. In this manner, surgical needle 14 can initially be secured and controlled within first jaw 56 and, upon closure of first and second jaws 56 and 58 and operation of toggle lever 70, control passed to second jaw 58 to enable surgical needle 14 to be secured therein. A loading lever 72 is provided on body portion 52 to enable surgical needle 14 to be loaded into first and second jaws 56 and 58. An exemplary example of surgical suturing apparatus 50 is disclosed in U.S. Pat. No. 5,674,229 to Tovey et al. the entire disclosure of which is incorporated by reference herein.

Figure 4A:
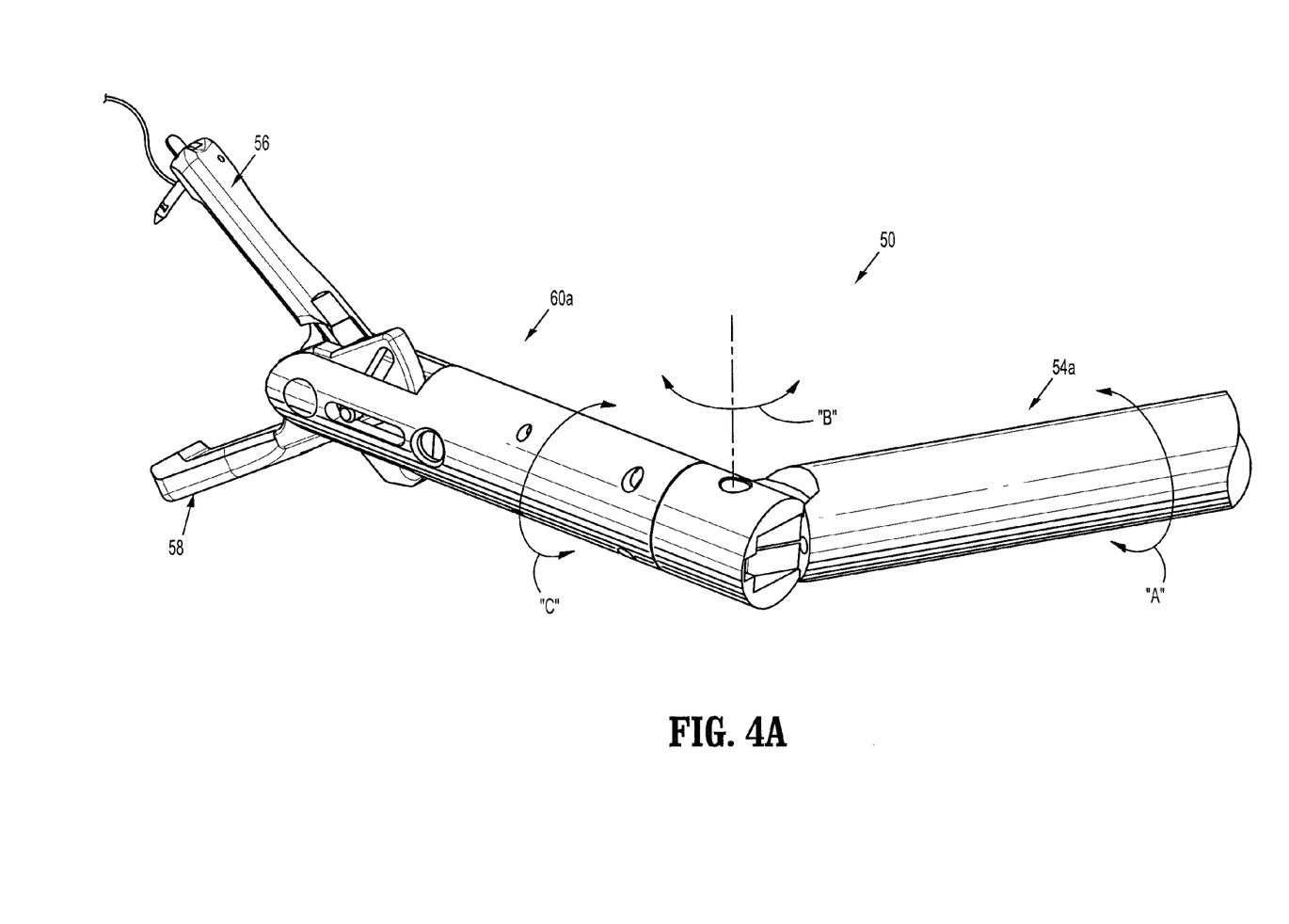
FIG. 4A is a perspective view of a distal end of a surgical suturing apparatus according to a further embodiment for use with the suture deployment system of FIG. 1.

As seen in FIG. 4A, surgical suturing apparatus 50 may include an elongate tubular member 54a having a distal end 60a that may be pivoted off-axis, in the direction of arrow "B" or opposite thereto, with respect to a longitudinal axis of tubular member 54a. It is further contemplated that distal end 60a may rotate about the longitudinal axis as indicated by arrows "C".

Figure 4B:
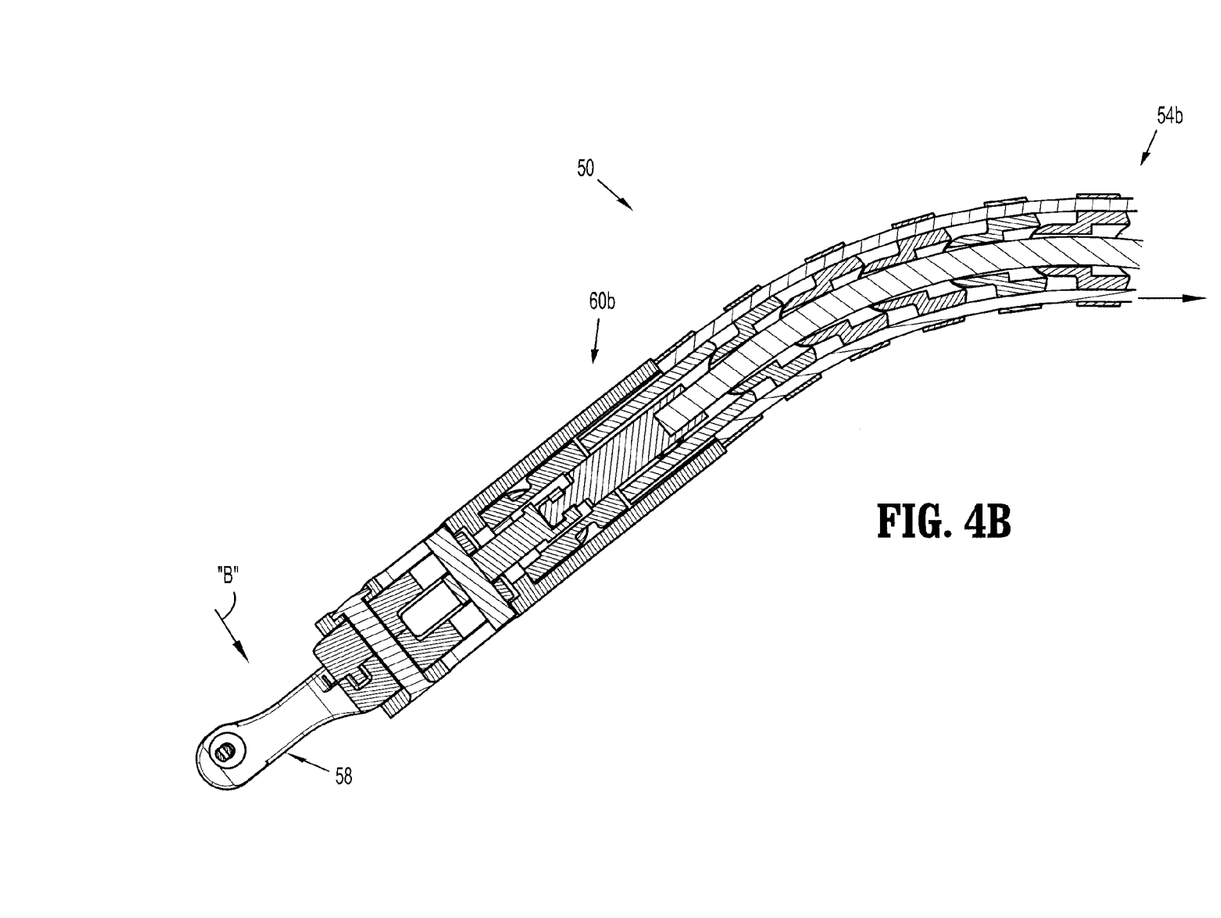
FIG. 4B is a perspective view of a distal end of a surgical suturing apparatus according to yet a further embodiment for use with the suture deployment system of FIG. 1.

As seen in FIG. 4B, surgical suturing apparatus 50 may include an elongate tubular member 54b having a distal end 60b that may be articulated off-axis, about a plurality of joints or the like.

Figures 5, 6:
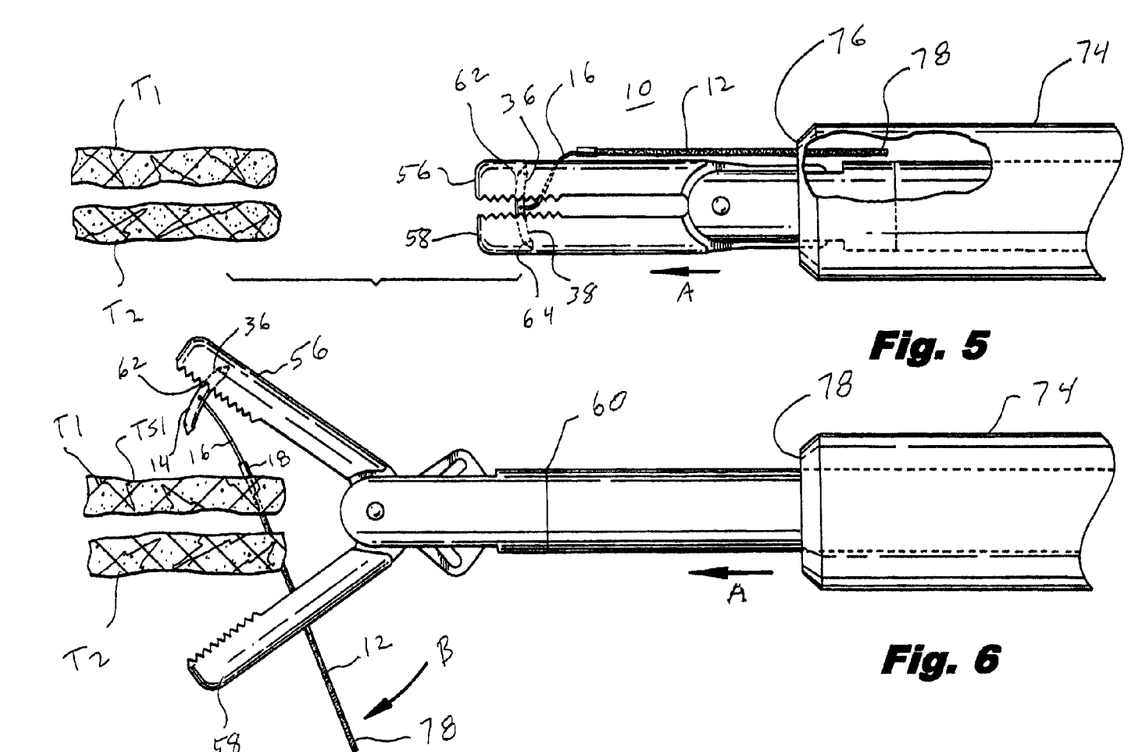
FIG. 5 is an enlarged side view, partially shown in section, of the surgical suturing apparatus of FIG. 4 advancing the suture deployment system through a cannula.
FIG. 6 is an enlarged side view, partially shown in section, of the surgical suturing apparatus positioning the suture deployment system about a pair of tissues.

Referring now to FIGS. 4-9, and initially with regard to FIG. 5, the operation of surgical suturing apparatus 50 and suture deployment system 10 to insert target suture 12 into tissue will now be described. Surgical needle 14 is initially positioned within first and second jaws 56 and 58 of surgical suturing apparatus 50 such that first pointed end 36 of surgical needle 14 is located within first needle hole 62 in first jaw 56 and second pointed end 38 of surgical needle 14 is located within second needle hole 64 in second jaw 58. Toggle lever 70 (FIG. 4) is actuated to secure first pointed end 36 of surgical needle 14 within first needle hole 62 in first jaw 56. While not specifically shown, this is accomplished by advancing engagement structure associated with first jaw 56 and toggle lever 70 into engagement with engagement slot 46 adjacent first pointed end 36 of surgical needle 14. Second pointed end 38 of surgical needle 14 is free to move in and out of second needle hole 64 in second jaw 58.

During various surgical operations, a cannula, such as, for example, a cannula 74 is inserted into the body cavity to provide access for surgical suturing apparatus 50. As noted hereinabove, suture deployment system 10 allows target suture 12 to be transported through cannula 74 without causing undue bending of target suture 12. Handles 66 and 68 of surgical suturing apparatus 50 are actuated to move first and second jaws 56 and 58 to the closed position. As shown, as first and second jaws 56 and 58 are advanced in the direction of arrow A through cannula 74 and out a distal end 76 of cannula 74. Flexible suture 16 enables target suture 12 to remain relatively straight and lie along first and second jaws 56 and 58 as target suture 12 is passed through cannula 74. As best shown in FIGS. 5 and 6, as target suture 12 is advanced in the direction of arrow A, a proximal end 78 of target suture 12 passes through cannula 74 and out and distal end 76 of cannula 74.

Referring now to FIG. 6, as proximal end 78 of target suture 12 clears distal end 78 of cannula 74, target suture 12 is free to fall down alongside first and second jaws 56 and 58 in the direction of arrow B as shown. Specifically, the flaccid nature of flexible suture 16 allows target suture 12 to remain relatively straight while flexible suture 16 bends during manipulation of surgical needle 14. Once proximal end 78 of target suture 12 has cleared distal end 76 of cannula 74, handles 66 and 68 of surgical suturing apparatus 50 (FIG. 4) may be manipulated to move first and second jaws 56 and 58 to an open position spaced apart from each other. Thereafter, open first and second jaws 56 and 58 may be positioned about a pair of relatively tough tissue sections such as, for example, tissue sections T1 and T2 to be sutured together. As noted hereinabove, surgical needle 14 is secured within first jaw 56. At this stage, flexible suture 16 extends from surgical needle 14 and is secured to target suture 12 by collar 18 as described hereinabove. Target suture 12 is now located adjacent first and second tissue sections T1 and T2 while collar 18 is substantially adjacent first tissue surface TS1 of first tissue T1.

Figure 7:
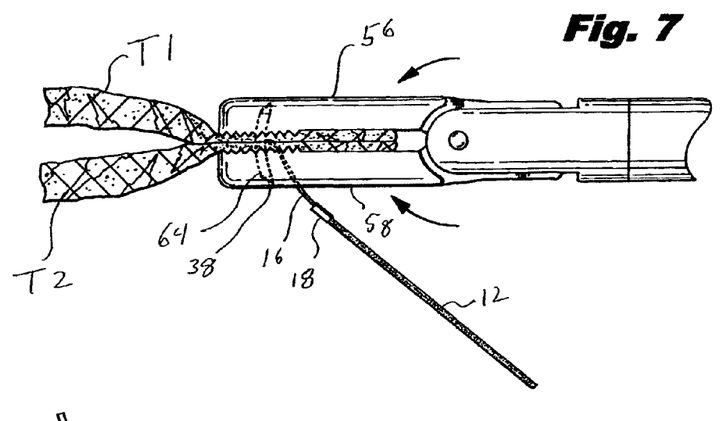
FIG. 7 is an enlarged side view, partially shown in section, of the surgical suturing apparatus driving a needle of the suture deployment system through the pair of tissues.

Referring to FIG. 7, once first and second jaws 56 and 58 have been properly positioned about first and second tissue sections T1 and T2, handles 66 and 68 are manipulated to bring first and second jaws 56 and 58 to a closed position adjacent each other. As first and second jaws 56 and 58 are moved to the closed position, surgical needle 14, and specifically, second pointed end 38 of surgical needle 14, pierces first and second tissue sections T1 and T2 and enters second needle hole 64 in second jaw 58. As shown, flexible suture 16 attached to target suture 12 by collar 18 is free to move along with the movement of surgical needle 14 without causing undue bending of target suture 12. Prior to opening first and second jaws 56 and 58, toggle lever 70 (FIG. 4) is operated to pass control of surgical needle 14 from first jaw 56 to second jaw 58. Specifically, surgical needle 14 is released from engagement with first jaw 56 and engagement structure associated with second jaw 58 engages second engagement slot 48 in surgical needle 14. Thus, surgical needle 14 is securely engaged within second hole 64 in second jaw 58.

Figure 8:
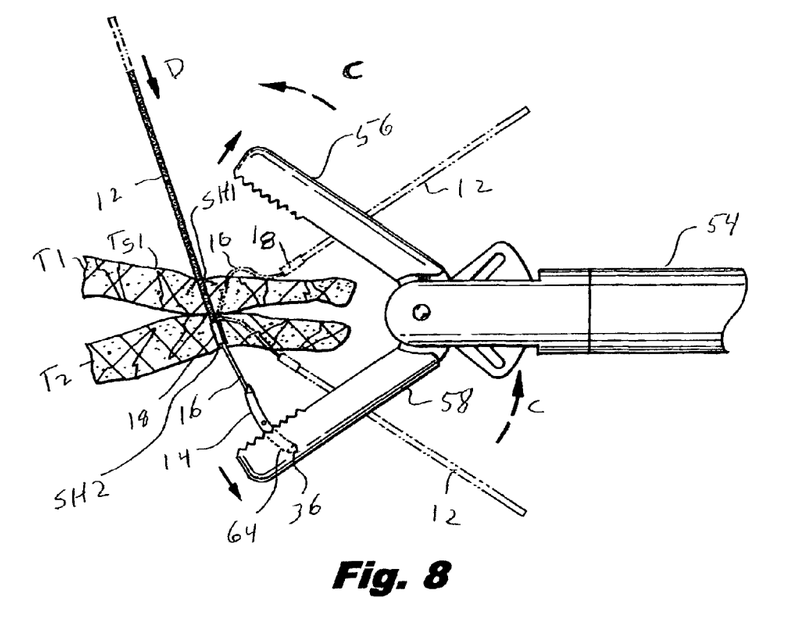
FIG. 8 is an enlarged side view, partially shown in section, of the surgical suturing apparatus pulling an intermediate suture, a sleeve and a target suture of the suture deployment system through the tissues.

As best shown in FIG. 8, once tissue sections T1 and2 have been pierced by surgical needle 14, handles 66 and 68 may be manipulated to move first and second jaws 56 and 58 to the open position spaced apart from each other. As shown, as first and second jaws 56 and 58 are moved to the open position, surgical needle 14 is drawn through first and second suture holes SH1 and SH2 formed through first and second tissue sections T1 and T2. Flexible suture 16 is also drawn through first and second suture holes SH1 and SH2. As flexible suture 16 is drawn through first and second suture holes SH1 and SH2, collar 18, fixed to flexible suture 16, is drawn along first tissue surface TS1 until collar 18 is located adjacent first suture hole SH1 in first tissue T1. Target suture 12, being relatively stiff in nature, tends to rise up from alongside first and second tissue sections T1 and T2 in the direction of arrow C. When collar 18 begins to be drawn through first suture hole SH1, relatively stiff target suture 12 "flips up" in the direction of arrow C and generally assumes a substantially perpendicular orientation relative to first tissue surface TS1. As surgical instrument 50 is further manipulated, second jaw 58 draws surgical needle 14, flexible suture 16, collar 18 and target suture 12 through first and second suture holes SH1 and SH2 in the direction of arrow D.

Figure 9:
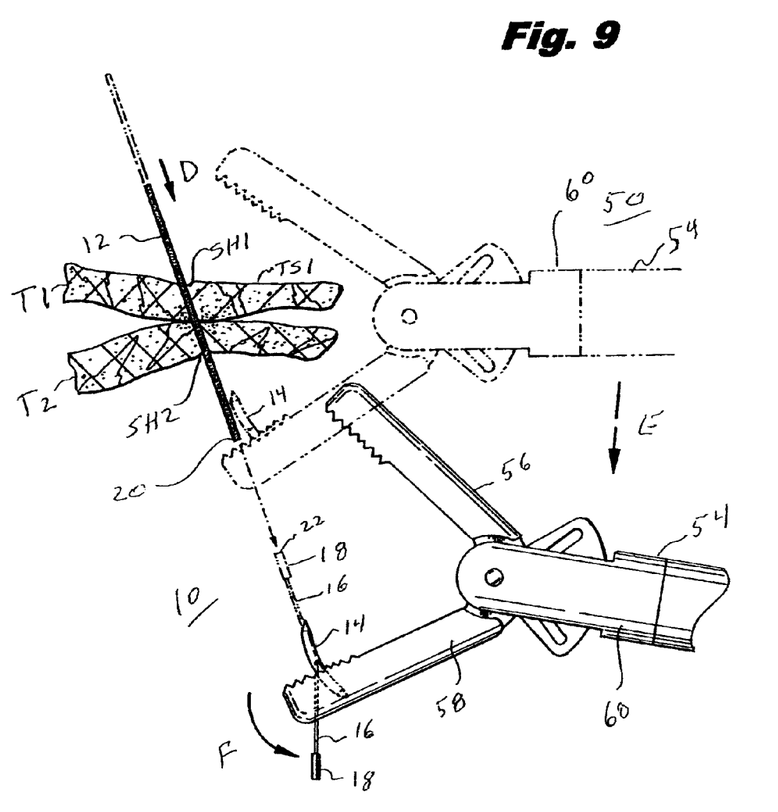
FIG. 9 is an enlarged side view, partially shown in section, of the surgical suturing apparatus pulling the target suture through the tissues.

Referring now to FIG. 9, once target suture 12 has been pulled through first and second suture holes SH1 and SH2 in first and second tissue sections T1 and T2, respectively, distal end 60 of elongate tubular member 54 is moved in the direction of arrow E to move second jaw 58 downwardly relative to first and second tissue sections T1 and T2 thereby drawing target suture 12 completely through first and second tissue sections T1 and T2 in the direction of arrow D. After target suture 12 has been fully seated within first and second tissue sections T1 and T2, further movement of second jaw 58 away from tissue sections T1 and T2 exerts further tension on surgical needle 14, flexible suture 16 and collar 18. Once a predetermined amount of tension has been achieved, distal end 20 of target suture 12 pulls free of proximal end 22 of collar 18 thereby releasing target suture 12 from the remainder of suture deployment system 10. Barbs 30 on outer surface 32 of target suture 12 facilitate securing target suture 12 within first and second tissue sections T1 and T2. The remainder of suture deployment system 10, including flexible suture 16 and collar 18 are free to fall down in the direction of arrow F alongside second jaw 58.

In this manner, suture deployment system 10 allows relatively stiff target suture 12 to be manipulated through cannula 74 and through tissue sections T1 and T2 without risk of bending or breaking target suture 12.

It will be understood that various modifications may be made to the embodiments disclosed herein. For example, various other types of target sutures may be deployed utilizing the disclosed suture deployment system. Further, the disclose suture deployment system may be provided with a variety of other types of surgical needles such as single pointed, straight, curved, etc. Additionally, other releasable means for securing the flexible suture to the target suture may be provided, such as, for example, adhesives, interlocking braids, welding, etc. Therefore, the above description should not be construed as limiting, but merely as exemplifications of particular embodiments. Those skilled in the art will envision other modifications within the scope and spirit of the claims appended hereto.

The invention claimed is:

1. A suture deployment system comprising:
  a surgical needle;
  a flexible suture having a distal end and a proximal end, the distal end of the flexible suture being attached to the surgical needle;
  a target suture having a distal end and a proximal end; and
  a collar releasably coupling the target suture with the flexible suture, wherein the distal end of the target suture is releasably secured to the collar through partial crimping of the collar about the distal end of the target suture, the proximal end of the flexible suture is fixedly secured to the collar through crimping of the collar about the proximal end of the flexible suture, and upon application of a tensile force along the suture deployment system, the distal end of the target suture releases from the collar and the collar remains fixed to the flexible suture.

2. The suture deployment system as recited in claim 1, wherein the target suture includes a plurality of barbs located on an outer surface of the target suture.

3. The suture deployment system as recited in claim 1, wherein the collar has a distal end and a proximal end, the collar being positioned intermediate the proximal end of the flexible suture and the distal end of the target suture.

4. The suture deployment system as recited in claim 3, wherein the distal end of the target suture is releasably secured within the proximal end of the collar.

5. The suture deployment system as recited in claim 3, wherein the target suture is a monofilament.

6. The suture deployment system as recited in claim 1, wherein the distal end of the flexible suture is secured within a suture hole formed in a body portion of the surgical needle.

7. The suture deployment system as recited in claim 6, wherein the suture hole is formed in a center of the body portion.

8. The suture deployment system as recited in claim 7, wherein the surgical needle is a double pointed needle having a tissue penetrating tip formed at each end of the body portion.

9. The suture deployment system as recited in claim 8, wherein the surgical needle includes engagement slots formed adjacent each tissue penetrating tip for receipt of an engagement structure associated with a surgical suturing apparatus.

10. The suture deployment system as recited in claim 6, wherein the distal end of the flexible suture is crimped within the suture hole formed in the body portion.

11. The suture deployment system as recited in claim 1, wherein the collar is formed of polymeric material.

12. The suture deployment system as recited in claim 1, wherein the collar is formed of stainless steel.

13. A suture deployment system comprising:
a surgical needle having a body portion and a tissue penetrating tip formed at each end of the body portion;
a multifilament suture having a distal end and a proximal end, the distal end of the multifilament suture being secured within a suture hole in the body portion of the surgical needle;
a hollow collar having a distal end and a proximal end, the proximal end of the multifilament suture being within the distal end of the hollow collar; and
a monofilament target suture having a distal end and a proximal end, wherein the distal end of the monofilament target suture is releasably secured within the proximal end of the hollow collar through partial crimping of the hollow collar about the distal end of the monofilament target suture, the proximal end of the multifilament suture is fixedly secured to the hollow collar through crimping of the hollow collar about the proximal end of the multifilament suture, and upon application of a tensile force, the distal end of the monofilament target suture is released from the hollow collar and the hollow collar remains fixed to the multifilament suture.

14. The suture deployment system as recited in claim 13, wherein the monofilament target suture is a barbed suture.

15. The suture deployment system as recited in claim 14, wherein the barb suture is a compound barb suture including:
an elongated body; and
at least one barb extending from the elongated body and defining an inner surface, the inner surface including:
a first portion disposed at a first orientation relative to a longitudinal axis of the elongated body; and
a second portion disposed at a second orientation relative to the longitudinal axis.

16. The suture deployment system as recited in claim 15, wherein at least one of the first and second portions is substantially linear.

17. The suture deployment system as recited in claim 16, wherein the first and second portions are at first and second angles relative to respective longitudinal axes of the elongated body.

18. The suture deployment system as recited in claim 16, wherein the second angle is less than the first angle.

19. The suture deployment system as recited in claim 16, wherein the first angle is between about 0 degrees to about 90 degrees.

20. The suture deployment system as recited in claim 16, wherein the first angle is between about 30 degrees to about 50 degrees.

21. The suture deployment system as recited in claim 16, wherein the second angle is between about 0 degrees to about 90 degrees.

22. The suture deployment system as recited in claim 16, wherein the second angle is between about 2 degrees to about 25 degrees.

23. The suture deployment system as recited in claim 15, wherein the inner surface of the at least one barb includes a third portion disposed at a third orientation relative to the longitudinal axis of the elongated body, wherein the third orientation defines a third angle that is between about 0 degrees to about 90 degrees.

24. The suture deployment system as recited in claim 23, wherein the third angle is between about 2 degrees to about 50 degrees.

25. The suture deployment system as recited in claim 13, wherein the surgical needle includes at least one crimping bump adjacent the suture hole.

26. The suture deployment system as recited in claim 13, wherein the surgical needle includes at least one engagement slot for receipt of an engagement structure associated with a surgical suturing apparatus.

* * * * *